(12) United States Patent
Forster et al.

(10) Patent No.: US 10,602,969 B2
(45) Date of Patent: Mar. 31, 2020

(54) METHOD OF REUSE PROTECTION FOR LANCET SYSTEM

(71) Applicant: Roche Diabetes Care, Inc., Indianapolis, IN (US)

(72) Inventors: Richard Forster, Fensterbach (DE); Susanne Gentsch, Viernheim (DE); Andreas Gorshöfer, Steinberg am See (DE); Michael Keil, Limburgerhof (DE); Thomas Weiss, Mannheim (DE); Robert Wessel, Schwarmstedt (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 203 days.

(21) Appl. No.: 15/848,437

(22) Filed: Dec. 20, 2017

(65) Prior Publication Data

US 2018/0132772 A1    May 17, 2018

Related U.S. Application Data

(60) Division of application No. 14/497,991, filed on Sep. 26, 2014, now Pat. No. 9,895,093, which is a division
(Continued)

(30) Foreign Application Priority Data

Feb. 17, 2009    (EP) .................................. 09002176

(51) Int. Cl.
*A61B 5/151* (2006.01)
*A61B 5/15* (2006.01)

(52) U.S. Cl.
CPC ........ *A61B 5/15153* (2013.01); *A61B 5/1411* (2013.01); *A61B 5/1518* (2013.01);
(Continued)

(58) Field of Classification Search
CPC .............. A61B 5/1411; A61B 5/15146; A61B 5/15186; A61B 5/15142; A61B 5/15134;
(Continued)

(56) References Cited

U.S. PATENT DOCUMENTS 4,442,836 A   4/1984  Meinecke et al.
4,990,154 A   2/1991  Brown et al.
(Continued)

FOREIGN PATENT DOCUMENTS

DE    10053974 A1   5/2002
EP     0565970 A1  10/1993
(Continued)

OTHER PUBLICATIONS

English Translation of International Search Report and Written Opinion of the ISA, PCT/EP2010/000876, dated Dec. 5, 2010, 15 pages.
(Continued)

*Primary Examiner* — Anh T Dang
(74) *Attorney, Agent, or Firm* — Bose McKinney & Evans LLP

(57) ABSTRACT

A lancet magazine for use in a lancing aid is described comprising a plurality of lancets each having a lancet body at the proximal end of the lancet and a lancet tip at the distal end of the lancet, where the proximal end of the lancet points in the direction of the proximal end of the housing of the lancet magazine and the distal end of the lancet is aligned in the direction of the distal end of the housing and the lancets in the unused state are completely surrounded by the housing. Furthermore, an extension unit is movably connected to the housing in such a manner that the housing can be extended by movement of the extension unit in the direction of the distal end of the housing such that the lancet is prevented from emerging from the lancet magazine.

14 Claims, 6 Drawing Sheets

Related U.S. Application Data of application No. 13/210,795, filed on Aug. 16, 2011, now Pat. No. 8,845,669, which is a continuation of application No. PCT/EP2010/000876, filed on Feb. 12, 2010.

(52) U.S. Cl.
CPC .... *A61B 5/150022* (2013.01); *A61B 5/15115* (2013.01); *A61B 5/15163* (2013.01); *A61B 5/15176* (2013.01); *A61B 5/150412* (2013.01); *A61B 5/150519* (2013.01); *A61B 5/150572* (2013.01); *A61B 5/150824* (2013.01)

(58) Field of Classification Search
CPC ............ A61B 5/15148; A61B 5/15151; A61B 5/15153; A61B 5/15163; A61B 5/15178; A61B 5/15182
See application file for complete search history.

(56) References Cited

U.S. PATENT DOCUMENTS

| | | | |
|---|---|---|---|
| 5,074,872 A | 12/1991 | Brown et al. | |
| 5,324,303 A | 6/1994 | Strong et al. | |
| 5,454,828 A | 10/1995 | Schraga | |
| 5,554,166 A | 9/1996 | Lange et al. | |
| 5,611,809 A | 3/1997 | Marshall et al. | |
| 5,628,765 A | 5/1997 | Morita | |
| 5,964,731 A | 10/1999 | Kovelman | |
| 6,228,100 B1 | 5/2001 | Schraga | |
| 6,852,119 B1 | 2/2005 | Abulhaj et al. | |
| 7,001,364 B1 | 2/2006 | Farhi | |
| 7,785,338 B2 | 8/2010 | Kuhr et al. | |
| 2002/0120216 A1 | 8/2002 | Fritz et al. | |
| 2003/0153939 A1 | 8/2003 | Fritz et al. | |
| 2004/0034318 A1 | 2/2004 | Fritz et al. | |
| 2004/0230216 A1 | 11/2004 | Levaughn et al. | |
| 2004/0260325 A1 | 12/2004 | Kuhr et al. | |
| 2005/0033340 A1 | 2/2005 | Lipoma et al. | |
| 2005/0038465 A1 | 2/2005 | Shraga | |
| 2005/0234494 A1 | 10/2005 | Conway et al. | |
| 2006/0116607 A1 | 6/2006 | Nakamura et al. | |
| 2006/0178600 A1 | 8/2006 | Kennedy et al. | |
| 2006/0264996 A1 | 11/2006 | LeVaughn et al. | |
| 2007/0009381 A1 | 1/2007 | Schulat et al. | |
| 2008/0082023 A1 | 4/2008 | Deck et al. | |
| 2008/0125800 A1 | 5/2008 | List | |
| 2008/0267822 A1 | 10/2008 | List et al. | |
| 2009/0163944 A1 | 6/2009 | Nagao et al. | |

FOREIGN PATENT DOCUMENTS

| | | |
|---|---|---|
| EP | 0595148 A1 | 5/1994 |
| EP | 0630609 A2 | 12/1994 |
| EP | 1459683 A1 | 9/2004 |
| EP | 1997435 A1 | 12/2008 |
| JP | 2005/253781 A | 9/2005 |
| JP | 2005/270679 A | 10/2005 |
| JP | 2007/185499 A | 7/2007 |
| JP | 2008/540005 A | 11/2008 |
| WO | WO 01/66010 A1 | 9/2001 |
| WO | WO 2005/018425 A2 | 3/2005 |
| WO | WO 2005/018454 A2 | 3/2005 |
| WO | WO 2005/018711 A2 | 3/2005 |
| WO | WO 2008/072414 A1 | 6/2008 |

OTHER PUBLICATIONS

English Translation of International Preliminary Report on Patentability, PCT/EP2010/000876, dated Aug. 23, 2011, 12 pages.

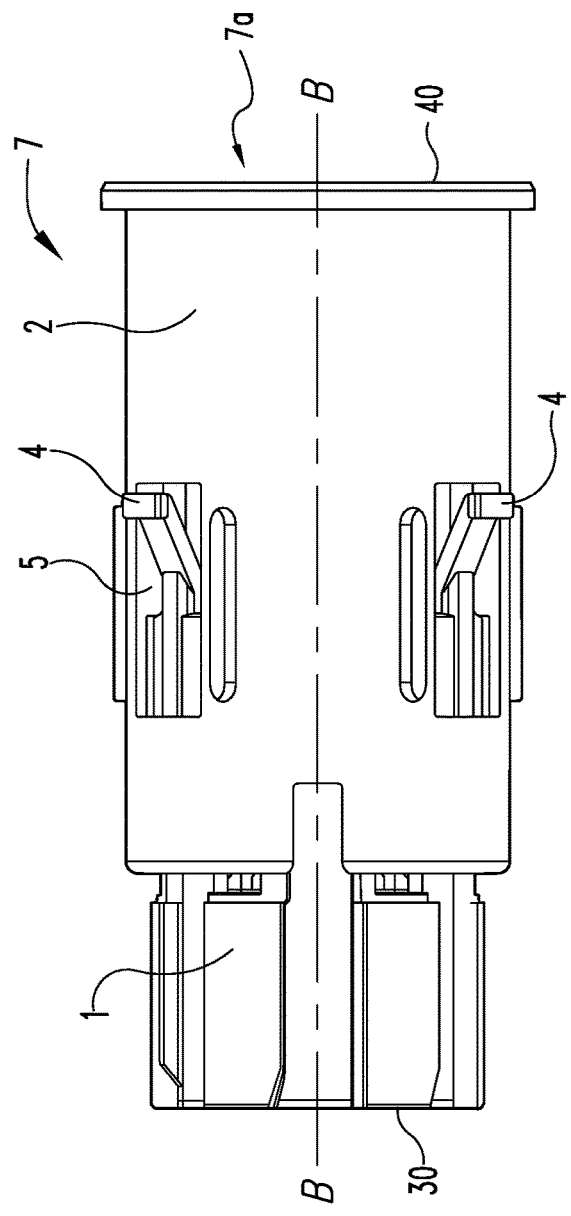
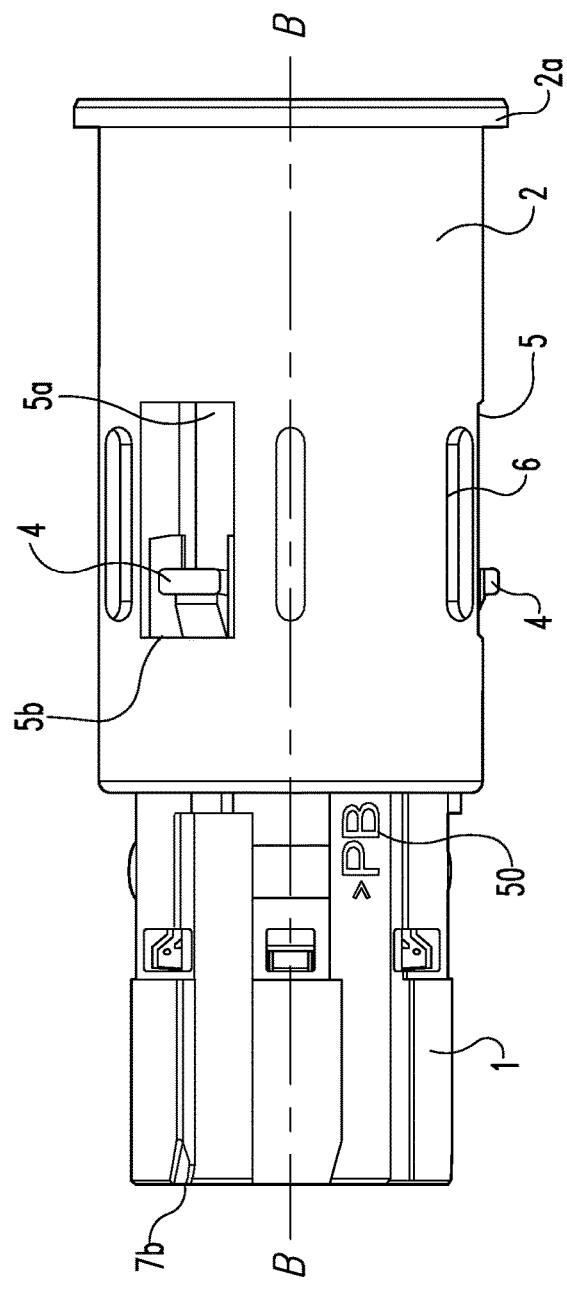
Fig. 1A
Fig. 1B

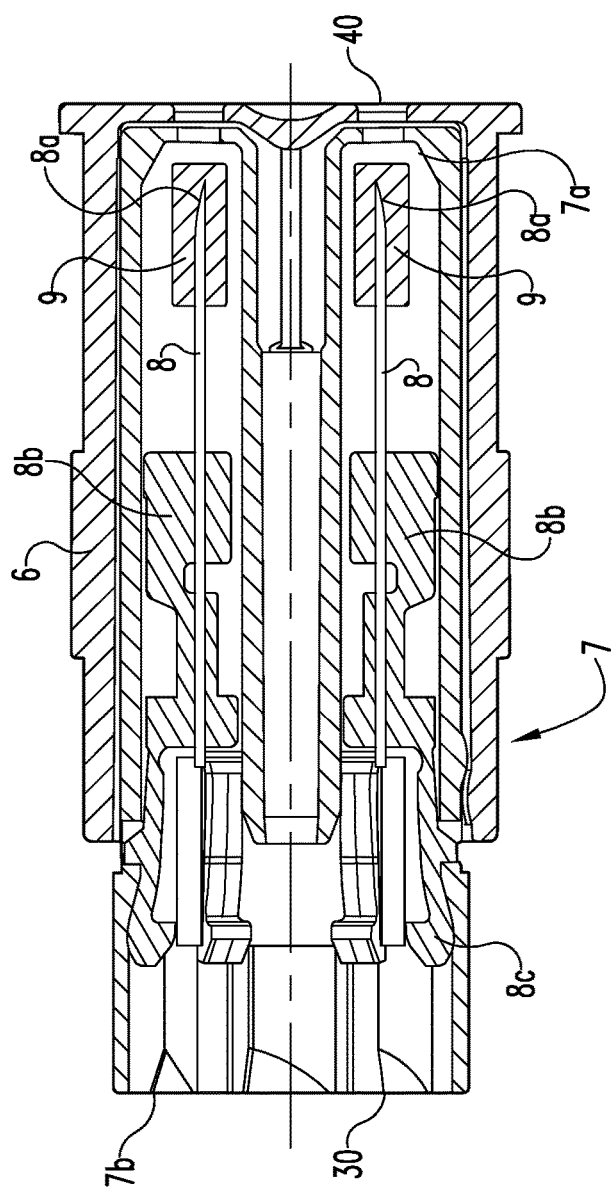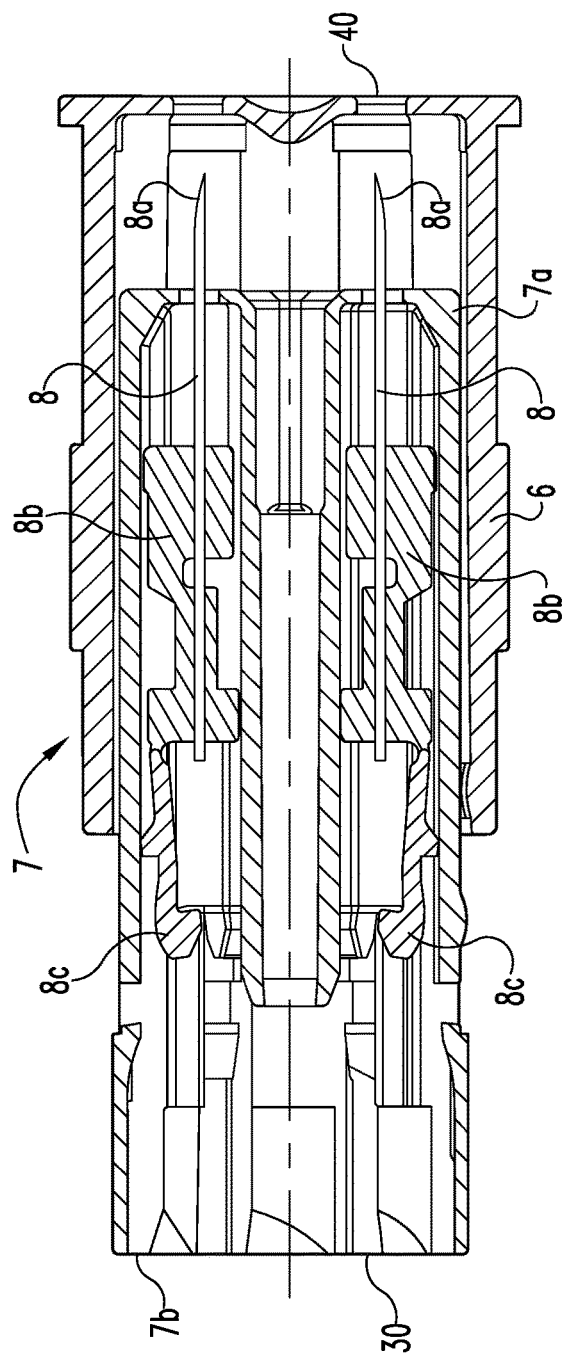
Fig. 3A
Fig. 3B

METHOD OF REUSE PROTECTION FOR LANCET SYSTEM

RELATED APPLICATIONS

This application is a divisional application of U.S. application Ser. No. 14/497,991, filed Sep. 26, 2014, now U.S. Pat. No. 9,895,093, which is a divisional application of U.S. application Ser. No. 13/210,795, filed Aug. 16, 2011, now U.S. Pat. No. 8,845,669, which is a continuation of International Application PCT/EP2010/000876, filed Feb. 12, 2010, which claims priority to EP 09002176.7, filed Feb. 17, 2009, all of which are hereby incorporated herein by reference in their entirety.

BACKGROUND

The present invention relates to a lancet system in the form of a lancet magazine which can be used in a lancing aid for collecting blood for diagnostic purposes.

In a variety of diseases it is necessary to examine human blood for an analyte contained therein. In many cases this only requires the withdrawal of a small amount of blood from the body in the form of a blood drop by producing a small puncture wound. A particularly important example of such a case is diabetes in which the glucose content of blood has to be examined at regular intervals. Blood may also for example be examined with regard to coagulation parameters, triglycerides, HbA1c or lactate. Blood lancet devices which consist of a lancing device and tailor-made replaceable lancets are usually used to produce the required puncture wounds. A lancet holder in which one interchangeable lancet can be inserted is present in the housing of the lancing device. During the lancing operation the lancet holder is rapidly moved in a lancing direction by a lancet drive which is also integrated into the lancing device until the lancet tip emerges from an exit opening provided at the front end of the lancing device and produces a small puncture wound in the part of the body that is pressed against the front end. Afterwards the lancet holder containing the lancet is moved back in the opposite direction to the lancing.

Small, easy to handle blood collection devices, so-called lancing aids that can be easily and reliably operated by the user and enable a part of the body to be lanced in a manner that is as pain-free as possible are now routinely used. In order to avoid infections especially in hospitals, the lancets are disposable elements intended for single use. After a lancet has been used once, the lancet is removed after the lancing operation or ejected from the device and discarded as refuse. In such a case the exposed lancets in a refuse container may lead to injury during waste disposal which may result in a contamination of other persons by the used lancet. Such contamination may lead to infections and thus some countries are planning to impose a ban on blood collection systems in which the needle tip is freely accessible after use. In addition to a risk of injury during waste disposal, there is also a risk that a used lancet may be accidentally re-used. This is particularly relevant for hospitals in which a lancing aid is used for several patients since such inadvertence of the nursing staff could lead to a patient being contaminated with the blood of a previous patient.

In addition to the use of blood lancet devices by medical staff, lancing aids are also used by laymen in the so-called home-monitoring field. This is particularly the case for monitoring the treatment of diabetics. Thus, it has been found in the treatment of diabetics that serious damage associated with diabetes such as loss of sight can be substantially reduced when the glucose concentration in the blood of the diabetic is determined frequently and up to five times daily and the insulin injection is exactly adjusted on the basis of these measurements. Lancing aids which enable the diabetic to carry out such a blood examination by himself are used for home-monitoring in order to carry out such frequent measurements. The resulting requirements for a blood lancet device are a simple handling when inserting new lancets and a reliable ejection of used lancets in addition to a simple handling when triggering the lancing operation and a relatively painless puncture. Lancet replacement should on the one hand be as simple as possible and, on the other and, ensure the utmost safety with regard to unintentional injury of the user or other persons. Although in the home-monitoring field it is conceivable that a lancet, once inserted, is used several times for lancing by the same user, even in this case an accidental re-use of an ejected lancet should be prevented once the user has decided to discard the lancet. Furthermore, other persons in particular should be reliably protected from the discarded lancets for example during waste disposal.

In the prior art the tip of the lancet is usually surrounded by a tip cover made of plastic when the lancet is inserted which allows a safe handling when the lancet is inserted. When the lancet is inserted, the tip cover is removed to expose the sharp tip of the lancet for the lancing operation. See, e.g., U.S. Pat. No. 5,628,765. However, due to the exposed lancet tip there is a risk of accidental injury and the tip may become damaged. The lancet is removed from the lancing aid after one or several lancing operations. This can either be carried out manually in which case there is a high risk of injury by the lancet tip or by an automatic ejection mechanism.

A blood lancet device is disclosed in EP 0 565 970 in which the lancet is ejected from the lancet holder by means of an ejecting rod. The user can operate the ejecting rod by pressing a corresponding button.

Furthermore, an ejecting mechanism is described in the patent document U.S. Pat. No. 4,442,836 where the lancet is automatically released when the lancing aid is retensioned so that the used lancet is discarded after each lancing operation. Such ejecting mechanisms require a relatively high degree of additional engineering. Moreover, multiple use of an already inserted lancet system is not possible, which is, however, often desired by customers especially in the home-monitoring field. Another major disadvantage of the described prior art is that the lancet tip is unprotected after the lancet has been ejected resulting in an associated risk of injury as described above.

In order to facilitate the safe removal of a used lancet, blood collection systems are also described in the prior art which ensure that the lancet tip is protected after ejecting the lancet. This is regarded as an essential feature especially for elderly users or those who are handicapped by poor sight and shaky or trembling hands as a result of disease.

A protection of the lancet tip is achieved in the prior art by integrating the lancet in a cap of the lancing aid such that the lancet and the housing cap together form a replaceable disposable unit. Such designs are described in the documents EP 0 595 148 and U.S. Pat. Nos. 4,990,154, 5,454,828 and U.S. Pub. No. 2004-0034318. When the lancet is ejected by the user, the housing cap is placed over the lancet tip so that the lancet surrounded by the cap can be subsequently discarded. Even if the lancet tip is protected after ejection by the described mechanism, it is nevertheless possible for a careless user to reinsert a lancet that has already been ejected once and carry out a new lancing operation. Consequently the user himself has to recognize that the lancet has already been used.

The document EP 0 630 609 discloses a mechanism which directly prevents reinsertion and thus re-use of a lancet that has been ejected once. The described lancet device comprises a lancet with a lancet body which breaks when the lancet is ejected from the lancing aid to prevent a reinsertion of the lancet. This prevents the user from re-using a contaminated lancet. However, a disadvantage of the prior art is that the lancet tip is unprotected after the lancet has been ejected.

For individual lancets there are a wide variety of solutions for protecting a user from the used lancet tip. Thus, various mechanisms are described in the documents U.S. Pat. Nos. 5,964,731, 7,001,364 and 5,454,828 relating to how a protecting mechanism can be brought over the lancet after use so that the lancet cannot be re-used. However, these mechanisms either have to be applied by the user himself which limits the effectiveness of the protection from injury or the mechanism is automatically triggered after each lancing operation by the lancing mechanism of the lancing aid as described in WO 2008/072414 so that the lancet can only be used once in an inserted state.

A protection against re-use is described in U.S. Pat. No. 7,785,338 which enables the housing of the lancet system to be changed after use of a lancet system in such a manner that it can no longer interact in a regular manner with a lancing aid. This is achieved by a change in the coupling site between the lancet magazine and lancing aid. In this case it is no longer possible to reinsert an already used magazine. This is intended to protect the user against re-using an already used lancet. However, a disadvantage of this prior art is that the coupling site of the lancing aid can be damaged when it is attempted to reinsert an already used magazine into the lancing aid if the user does not immediately recognize that the magazine no longer correctly fits the coupling site of the lancing aid.

SUMMARY

The present invention provides an easy to handle lancet magazine preferably for the home-monitoring field which can interact with a lancing aid in such a manner that the re-use of an already ejected lancet magazine is prevented, without affecting the interaction of the lancet magazine and the lancing aid and at the same time ensuring at all times a protection from injury from the lancet tip when the lancet magazine is used. Multiple use of a lancet of a lancet magazine that has been inserted only once is advantageously possible.

The embodiments disclosed herein concern a lancet magazine and a lancet system having a lancing aid and a lancet magazine. Also disclosed is a securing system for securing the lancets in the lancet magazine or the lancet system.

The lancet magazine for use in a lancing aid comprises a housing having a distal and a proximal end and at least one cavity for storing lancets. A plurality of lancets each having a lancet body at the proximal end of the lancet and a lancet tip at the distal end of the lancet which is suitable for generating an opening in the skin, are located in the lancet magazine. The proximal end of at least one lancet points in the direction of the proximal end of the housing and the distal end of the lancet is aligned in the direction of the distal end of the housing. The proximal end of the lancet magazine housing is preferably designed such that it can interact with a lancing aid. This interaction can be characterized by the magazine holder or by the design of the proximal end allowing entry of a drive element of the lancing aid, e.g., in the form of an opening or recess in the lancet magazine housing. The lancets are completely surrounded by the housing in the unused state. This ensures that whenever the lancet magazine is used the user cannot be injured by the lancets. The lancet is only moved into a deflected state by the drive mechanism of the lancing aid and can puncture the skin of the user when it is in the withdrawal position.

Furthermore, the lancet magazine has an extension unit which is movably connected to the housing of the lancet magazine. The extension unit can move in the direction of the distal end of the magazine housing such that the housing can be extended by the extension unit in the direction of the distal end of the housing and can thus prevent the lancet from emerging from the lancet magazine. As a result the lancet does not emerge from the lancet magazine even when a lancing mechanism is triggered and even if the lancet magazine is correctly inserted into the lancing aid. There is preferably a lancet in each cavity. The cavities can be separated from one another by cavity walls. It is, however, also conceivable that the cavity is the void around each lancet and that they are only separated from one another by a groove or notch on the lancet magazine. The cavity may also be a hollow space in which at least two lancets are located which are at a defined distance from one another. After the lancet magazine has been extended, the lancet cannot emerge from the extended lancet magazine housing even if the lancet magazine has been correctly coupled with the lancing aid.

Consequently the lancet magazine has two elements which are interconnected in such a manner that they can move relative to one another. The elements are the lancet magazine housing itself and the extension unit. These two elements are arranged relative to one another in such a manner that the lancet magazine can be selectively converted from an unextended state into an extended state. There are no constraints on the shape and design of the two elements provided they are arranged movably in relation to one another such that in the unextended state at least one of the lancets in the lancet magazine housing can be at least partially moved out of the lancet magazine housing and that in the extended state of the lancet magazine the lancet cannot emerge from the lancet magazine. During the extension process the extension unit is preferably moved parallel to at least one lancet in the lancet magazine. This is the lancet which is located in a removal position in the lancet magazine or lancet system. This removal position is defined relative to the lancet magazine such that the lancet magazine housing has an opening at the distal end through which the lancet can pass. In relation to a lancing aid into which the lancet magazine can be inserted, the removal position is characterized such that a drive element (e.g., a plunger) can interact with one of the lancets in the lancet magazine such that this lancet is movably supported in the lancet magazine for a lancing operation. The extension of the lancet magazine in the direction of the longitudinal axis of the lancet in the removal position ensures that the lancet cannot emerge from the lancet magazine even when it is deflected by a lancing aid.

The extension unit as well as the lancet magazine housing can be manufactured from plastic material but other materials such as sheet metal are also conceivable. The lancet magazine housing preferably has a drum-like shape. Other shapes such as cuboid, cylindrical or disk-shaped structures are also conceivable. In this case the lancet magazine has at least one opening which allows at least one lancet to emerge from the lancet magazine housing during a lancing operation in the unextended state of the lancet magazine. In this process at least part of the lancet but at least the lancet tip protrudes from this opening. The extension unit which is movably connected to the lancet magazine housing at least in the area of the opening is located around at least part of the lancet magazine housing either within or outside the lancet magazine housing. It can be connected by means of guide grooves. The extension unit is preferably located outside the lancet magazine housing and matches the shape of the lancet magazine housing in at least two dimensions. In this connection the extension unit has a form fit with the lancet magazine housing. Furthermore, the movement of the extension unit is restricted in both directions of movement to prevent the extension unit from unintentionally slipping from the lancet magazine housing. This restriction can, on the one hand, be achieved by guide elements such as a groove and notch whose shape and lengths are matched to one another in such a manner that movement along one axis is restricted. On the other hand, the extension unit can be tapered at one end relative to the dimension of the lancet magazine housing so that a restriction of movement is achieved by the tapering. Since the aim is to be able to align or move the extension unit selectively relative to the lancet magazine housing such that the lancets do not emerge from the lancet magazine in the extended state even when they are deflected, it should be possible to move the extension unit at least in the direction of the opening of the lancet magazine housing in order to prevent the lancet from emerging from the lancet magazine in the removal position in the case of an intentional or unintentional lancing operation. The extension unit preferably has a length in its dimension in the direction in which the extension takes place which corresponds to at least the length of the part of the lancet which comes out of the lancet magazine housing during a regular lancing operation. However, the extension unit may also be longer. However, at least the length of the exiting part of the lancet should be covered by the extension unit in the extended state during a normal lancing operation.

Consequently, the lancet magazine is rendered unusable by the movement of the extension unit and at the same time the user is additionally protected against unintentional puncturing because the lancets are completely surrounded by the lancet magazine. The extension of the lancet magazine in the distal direction ensures that the proximal side of the magazine that can interact with a lancing aid is not impaired. This prevents reuse of the lancet magazine after extension of the magazine without impairing the insertion of the magazine. This has the advantage that if a used lancet magazine is accidentally inserted into the lancing aid, the docking site between the lancet magazine and lancing aid is not impaired. This prevents the lancing aid, which should be available for many years for the user, from being manipulated or damaged by a modified lancet magazine and rendered unusable, as is the case in EP 1 459 683 (U.S. Pat. No. 7,785,338) in which the lancet magazine is modified at the proximal end of the magazine to prevent reinsertion.

The extension unit can be moved automatically when the magazine is removed from the lancing aid. This can for example be carried out by means of an automatic ejection mechanism of the lancing aid which is actuated by the user once the magazine has been consumed. However, the extension unit can also be moved manually by the user along the lancet magazine when the magazine is manually removed from the lancing aid. In this case the lancet magazine housing and the extension unit are connected together in the unextended state such that the extension unit can only be transferred into the extended state when a certain application of force has been exceeded. This can for example be achieved by means of the fact that parts of the lancet magazine housing and of the extension unit are so closely mounted together that a certain frictional force has to be overcome until it is possible to move the extension unit. This securing of the unextended state can alternatively be accomplished by elements on the lancet magazine housing and extension unit such as for example notches or projections which rub against one another or hook into each other or lock into each other. A similar locking also takes place in the extended state of the lancet magazine.

In one embodiment the magazine can be inserted into the lancing aid in such a manner that the user can also remove the magazine without actuating the extension mechanism. This enables the user to also remove a lancet magazine from the lancing aid which has not been completely used up without it being made unusable by the extension. This can be achieved either by means of the fact that the extension unit extends within the lancet magazine housing and only protrudes from the distal end of the lancet magazine housing and can then be gripped in order to carry out the extension process. In an alternative embodiment the lancet magazine housing can be stretched out such that it is mounted in the inserted state within a lancing aid in such a manner that it can be gripped by the user so that the user is not able to handle the extension unit in order to remove the lancet magazine from the lancing aid and thus trigger the extension mechanism but can rather grip the lancet magazine housing itself and remove the lancet magazine without using the extension mechanism.

Furthermore, it is possible to use the lancet which is located in the collecting position in the lancet system several times. Hence, the user can select how often he uses each lancet before he moves a new lancet into the collecting position, e.g., by advancing the magazine in the lancing aid. However, the extension process can also be carried out on the lancet magazine without the magazine being inserted into the lancing aid.

The lancet magazine can also be inserted at any time into the lancing aid even in the extended state. In this case the proximal end of the lancet magazine housing can be inserted into the lancing aid to enable a correct interaction between the lancing aid and magazine. The lancing operation as such in which the drive unit interacts with the lancet and moves the lancet within the lancing aid can be also executed without, however, the lancet emerging from the lancet magazine.

The extension unit may interact with the housing after it has moved in the distal direction relative to the housing of the lancet magazine, i.e., in the extended state so that it cannot again be manually moved in the proximal direction of the housing. This can be achieved by a locking between the extension unit and lancet magazine housing. Interaction of two notches or of a groove and notch, one on the extension unit and one on the lancet magazine housing, are examples of such a locking of the two elements. This prevents the extension unit from moving again by itself into its original length in the unextended state.

These teachings additionally concern a lancet system for carrying out a lancing operation in a body comprising a lancing aid with a housing and a drive mechanism for a lancet as well as a receiving opening for a lancet magazine, a lancet magazine with a housing, which has a distal and a proximal end, comprising at least one lancet, the lancet having a tip at its distal end and its distal end pointing in the direction of the distal end of the lancet magazine, an extension unit which is movably connected to the housing of the lancet magazine.

The lancet magazine can be extended by the extension unit in the direction of the distal end of the housing thus preventing the lancets from emerging from the lancet magazine when it interacts with the lancing aid. In this process the proximal end of the lancet magazine is inserted into the lancing aid because the proximal end of the magazine is preferably designed so that it can interact with the lancing aid in such a way that it is held.

An aspect of these teachings is a lancet magazine that can be removed from the drive unit and which contains at least one lancet, the lancet magazine being provided as a disposable unit. In this connection the term lancet encompasses a blade-shaped, flat lancing unit as well as other conceivable embodiments. In principle lancets as they are basically well-known in the prior art and are used in lancet systems can be used within the scope of these teachings. In this connection a combination of a lancet with a base body which can couple to the lancing aid is frequently referred to as a lancet in the prior art. Such lancets often have a base body made of plastic in which a metal lancet is disposed. According to these teachings it is possible to integrate such a lancet into the lancet magazine or system. It is for example conceivable that the lancet body contains a base body like that used for lancets in the prior art, where the inventive functionality of the system is maintained by integration of the base body. In this case the lancet body has an at least two-part design according to the described embodiment. The lancet and the base body can then be guided in a movable manner within the magazine. The lancets within the lancet magazine can be present in separate cavities in order to prevent contamination of unused lancets by used lancets when reloading.

In order to carry out a lancing operation, portions of the lancet body are advantageously designed like the system already described in U.S. Pub. No. 2004-0034318 such that the individual lancets of the system can be actively coupled to the drive unit of the lancing aid. Embodiments that can also be used to drive lancets within a magazine of a lancing aid are described for example in the documents DE 10053974, U.S. Pat. Nos. 4,990,154 and 5,074,872. The chambers arranged next to one another in which the lancets are individually located are positioned successively relative to the drive unit in order to carry out a lancing operation in such a manner that in each case a single lancet can be coupled to the plunger of the drive unit. Also in this case, magazines in the form of a drum containing chambers in which the lancets are located parallel to the longitudinal axis of the drum have also proven to be particularly advantageous. The lancets preferably have additional lancet body arms on their lancet body which can interact with the drive unit of the lancing aid in such a manner that a form-fitting connection can take place between the drive unit (e.g., in the form of a plunger) and the lancet so that a guided movement of the lancet can take place during the lancing operation.

The lancet system can comprise a lancing aid with an attachable cap which can be removably connected to the housing of the lancing aid. After the extension operation of the lancet magazine by movement of the extension unit relative to the lancet magazine housing in which the extension unit is moved in the direction of the distal end of the housing of the lancet magazine, the cap can no longer be properly connected to the housing of the lancing aid. This is a further indication for the user of the lancing aid that the lancet magazine that he wants to use in the lancing aid has already been used.

In addition, a method for avoiding reuse of a lancet magazine is described in which the unused lancet magazine containing at least one lancet is placed in a lancing aid where the lancet magazine can again be removed from the lancing aid and a movable extension unit on the lancet magazine is moved in the direction of the distal end of the lancet magazine.

The lancets in the lancet magazine can be secured by securing means against a movement relative to the lancet magazine housing caused by accidental application of force. Such an accidental application of force can for example be that the lancet magazine alone is dropped or is dropped in combination with a lancing aid in which the lancet magazine is fitted.

This securing means can for example be a plastic sheath around the lancet tip. This sheath can be pierced when sufficient force is exerted on the lancet by a lancing aid.

This sufficient exertion of force occurs for example during a normal lancing operation in which the drive unit of the lancing aid, e.g., in the form of a plunger, is moved onto the lancet and the tip of the lancet is driven out of the housing of the lancing aid by this force impact in a guided movement. In contrast, the force exerted when a lancet magazine drops from a height of for example 2 m is not sufficient to pierce the plastic material. The threshold at which the force exerted is sufficient to pierce the plastic can be influenced by the selection of the composition of the plastic. U.S. Pub. No. 2003-0153939 describes how such a plastic can be constructed and how it can be connected to the lancet in such a manner that it fulfills the function of a sterile protection as well as a means for securing the lancet in the case of a fall.

In addition, the lancet system can also have a lancet holder for securing lancets in a lancet magazine in which case the lancing aid has a cavity for receiving a lancet magazine, and the lancing aid has a removal position in which a drive element can interact with one of the lancets in the lancet magazine such that this lancet is movably supported in the lancet magazine for a lancing operation. In this connection the lancing aid additionally has a securing element which prevents movement of the lancets which are not positioned in the collecting position. This securing element is preferably designed in the form of a pin which at least partly penetrates into the lancet magazine when the lancet magazine is inserted into the lancing aid. When the lancet magazine is inserted into the lancing aid, this pin is positioned relative to the lancet magazine in such a manner that the lancet body arms of the lancets which are not in the collecting position are secured in a recess of the lancet magazine housing. The lancet which is in the collecting position is for example secured by the plunger of the drive unit of the lancing aid by means of the fact that the lancet body arms and the plunger make a form-fit. The pin preferably has an elongate pen shape and thus advantageously has a round shape. Due to the round shape it creates less resistance when the lancet magazine is inserted into the lancing aid. The selective securing of only the lancets that are not in the collecting position is for example accomplished in that the pin is at least partly asymmetrically inserted into the lancet magazine. Alternatively the pin can have a recess for the drive element of the lancing aid which is moved parallel to the pin in the housing of the lancing aid during the lancing operation. This securing means protects the lancets in the lancet system or in the lancet magazine from unintentional displacement. An unintentional displacement of the lancets would for example be that the lancing aid together with the lancet magazine is dropped. Falls from greater heights, e.g., from up to heights of 3 m can be absorbed by this mechanism without the risk that a lancet accidentally emerges from the lancing aid or the lancet magazine. As a result the risk of injury due to incorrect operation of the lancing aid is largely eliminated.

One feature of the lancet system is the sterility of the lancet tip which is provided to produce a wound in an appropriate part of the body. The sterility of the lancet tip has to be ensured over a long period which extends from the manufacture of the lancet system up to its use. Sterility can be achieved during the manufacture of the lancet system by for example gamma radiation which is commonly used in the prior art. In order to maintain sterility, the lancet system can be sealed in a wrapping for example a polyethylene bag. In another embodiment the opening of the lancet system where the lancet tip emerges from the protective portion of the lancet body can for example be closed by a sealing foil. These are preferably detachable sealing foils which the user removes before using the lancet system. However, it is also possible to use thin foils which are not pierced by the lancet tip until the lancet is used so that the user does not have to carry out additional handling steps. Such foils may already be used as an integral part of the manufacturing process for the lancet system which is usually by means of an injection molding process.

Furthermore, in the prior art an elastomer is described in the application WO 01/66010 for sterile protection which encloses the lancet tip and thus protects it against contamination. This sterile protection can either be pierced during the lancing operation or be removed by the operator before use.

In an advantageous embodiment the protective portion of the lancet body can comprise a sterile protection and/or the protective portion can be essentially formed thereby. In this case the elastomer of the sterile protection itself serves for example as the protective portion of the lancet body by the fact that the lancet tip can be moved in a guided manner relative to the elastomer. In this process the sterile protection reversibly exposes the lancet tip or surrounds it again as for example in the case of an elastomer protection (US Pub. No. 2003-0153939) in which the elastomer is firstly pierced during the lancing operation and subsequently the lancet tip is retracted into the elastomer. Consequently in this example the lancet tip changes its position relative to the sterile protection during the lancing operation and the lancet tip is protected in its resting position after the lancing operation. In principle many embodiments of a sterile protection are conceivable and hence the inventive system is not limited to any special embodiment of a sterile protection.

DESCRIPTION OF THE FIGURES

The above-mentioned aspects of the present invention and the manner of obtaining them will become more apparent and the invention itself will be better understood by reference to the following description of the embodiments of the invention, taken in conjunction with the accompanying drawings, wherein:

FIG. 1A is a side view of a lancet magazine with an extension unit in the unextended state;

FIG. 1B is a side view of the lancet magazine of FIG. 1A with an extension unit shown in the extended state;

FIG. 3A is a sectional view of the lancet magazine from FIG. 2A along a line of intersection A-A;

FIG. 3B is a sectional view of the lancet magazine from FIG. 2B in a longitudinal section along the line of intersection A-A from FIG. 2B;

DETAILED DESCRIPTION

Figure 2A:
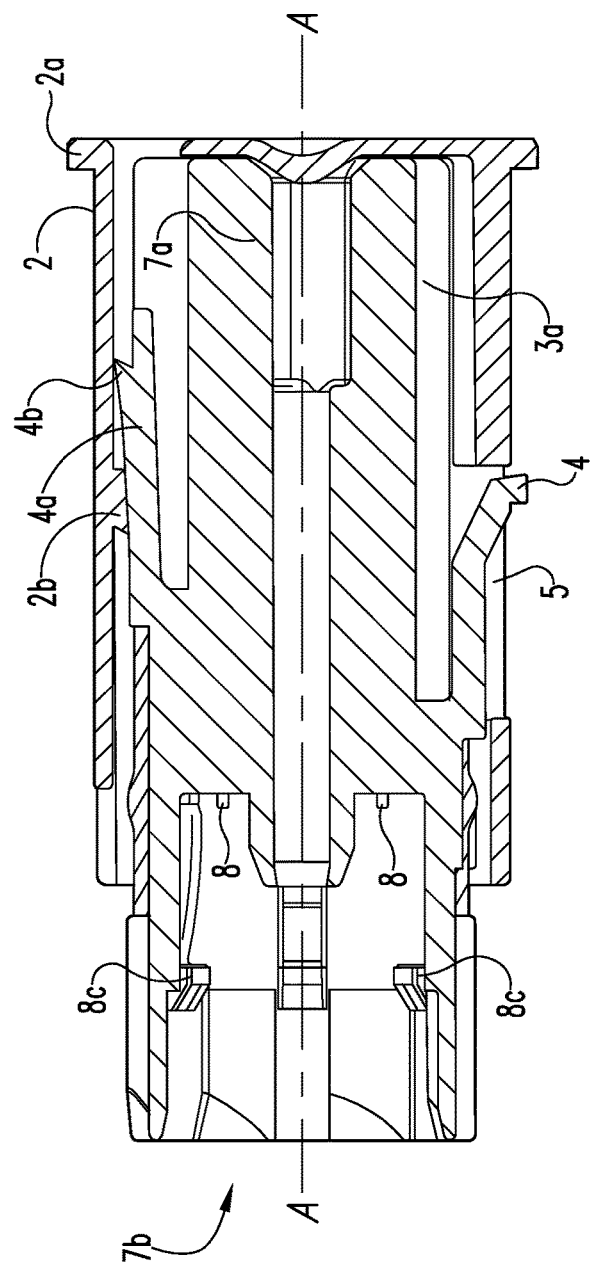
FIG. 2A is a longitudinal sectional view of the lancet magazine of FIG. 1A taken along line B-B.

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

The lancet magazine (7) shown in FIGS. 1 to 5 has a cylindrical shape which, however, does not mean that the magazine cannot also have any other shape, such as for example a box-like or cuboid shape. The cylindrical shape of the lancet magazine (7) shown here enables the lancets to be stored in the longitudinal direction of the cylindrical housing (1). Hence, the lancets lie parallel to one another in the housing (1).

FIG. 1A shows a lancet magazine (7) with a housing (1) which completely encloses the stored lancets (not shown in FIG. 1A). The lancet magazine (7) has an opening (30) at one end (the proximal end) through which a lancing aid (not shown in FIG. 1A) can interact with the lancets in the inside of the lancet magazine (7). There is likewise at least one opening (40) on the opposite side (the distal end) of the lancet magazine (7) which enables a lancet to exit from the magazine (7) during the lancing operation. The lancet magazine (7) additionally has an extension unit (2) which is movably connected to the housing (1). This extension unit (2) preferably also has a cylindrical design and is longitudinally aligned parallel to the housing of the lancet magazine (2) where at least part of this extension unit movably interacts with the housing (1). In the embodiment of FIGS. 1 and 2 the extension unit (2) spans a part of the lancet magazine housing (1) in its longitudinal extension and protrudes from the lancet magazine housing (1) at the distal end of the lancet magazine housing (1). This distal end of the extension unit (2) has a handle edge (2a) which is in the form of a thickening of the cross-section of the extension unit (2). Furthermore, the extension unit (2) has at least one lateral slot (5) and at least one guide (6) on its longitudinal side. The side slot (5) serves to receive a latch arm (4) which is attached to the lancet magazine housing (1). The latch arm (4) moves during the process of extending the lancet magazine housing (1) through the extension unit (2) from the distal end of the side slot (5a) to the proximal end of the side slot (5b) so that the latch arm (4) prevents the extension unit (2) from being moved further beyond the lancet magazine housing (1). Hence, it limits the extension displacement so that the extension unit (2) cannot be completely removed from the lancet magazine housing (1). Consequently the latch arm (4) can be seen at the upper (distal) end of the side slot (5a) in FIG. 1A, whereas after extension of the lancet magazine (7) it is found in FIG. 1B at the proximal end of the side slot (5b). Furthermore, the extended lancet magazine (1) from FIG. 1B has an optical mark (50) in the form of letters. This optical mark (50) can, however, also be designed in the form of a colored mark preferably on the lancet magazine housing (1).

Figure 2B:
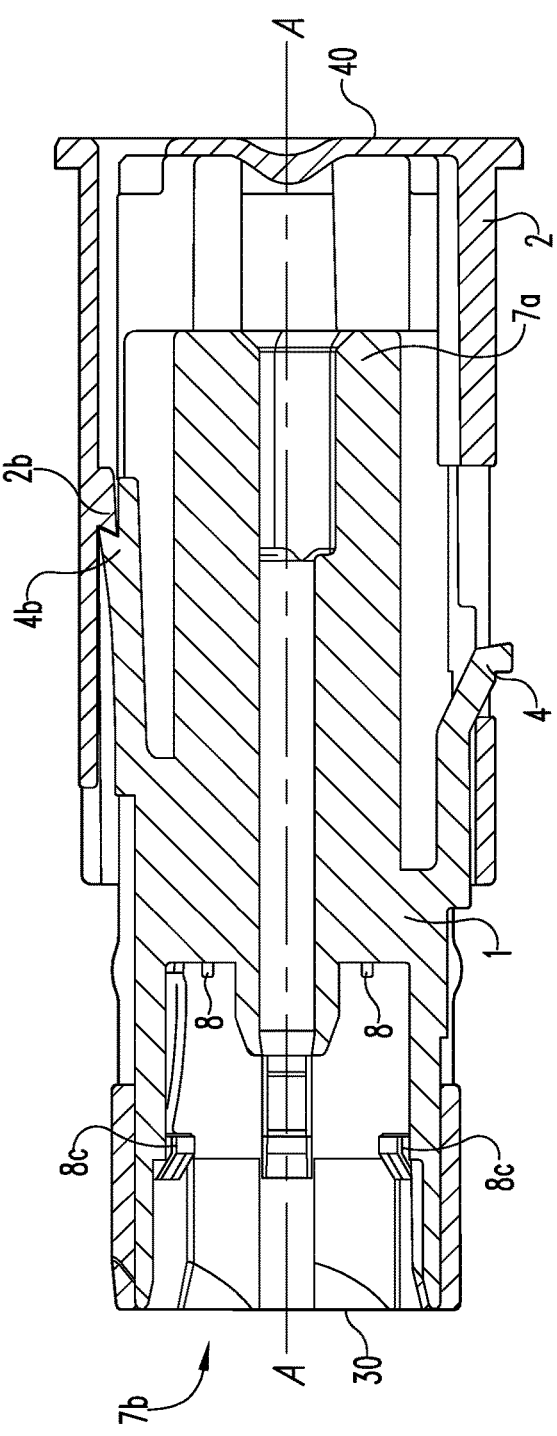
FIG. 2B is a sectional view of the lancet of FIG. 1A taken along line B-B and showing the lancet magazine in the extended state.

A cross-section of the lancet magazine (7) from FIG. 1A is shown in FIG. 2A in the line of intersection B-B. This view shows the arrangement of the latch arm (4) within the lancet magazine housing (1) where one end of the latch arm protrudes out of the side slot (5) of the extension unit (2). An additional latch arm (4a) is attached to another position of the lancet magazine housing (1) and is arranged within the extension unit (2). This latch arm (4a) has a notch (4b) which can interact with the notch (2b) of the extension unit (2) during an extension operation of the lancet magazine housing (1) in such a manner that the lancet magazine housing (1) can no longer be shortened as shown in FIG. 2B. In this case this is achieved by beveling the notches (4b) and (2b) in opposite directions so that these two elements are locked together in a form-fitting manner. The magazine housing (1) and extension unit (2) can also interact in other ways to prevent a return movement after the extension phase. Thus, it would also be conceivable that the notch (4b) engages in a groove of the extension unit (2) and is locked into position there. During the extension process, the inner latch arm (4a) is pressed by the notch (2b) into the inside of the lancet magazine until the notch (5b) has slid past the notch (4b). When the two notches slide past each other a certain frictional resistance is built up which has to be overcome during the extension process. This ensures that the lancet magazine (7) does not become extended by itself or by a small exertion of force in its longitudinal direction by moving the extension unit (2) against the lancet magazine housing. Although the inserted lancets (8) cannot be completely seen in this view of FIGS. 2A and 2B because they are covered by a cavity boundary (3a), it is at least possible to see the lancet body arms (8c) of two lancets (8) below the cavity boundaries (3a).

FIG. 3A shows the stored lancets (8) with the lancet tips (8a) as well as the lancet bodies (8b) and the lancet body arms (8c) in the sectional plane A-A of FIG. 2A. In addition a sterile protection (9) which surrounds at least the lancet tip (8a) is shown in this sectional view. This sterile protection (9) serves to keep the lancet tip (8a) sterile during the storage phase and can be held back by the lancet opening (40) during the drive operation of the lancet (8) wherein a plunger of the lancing aid can interact with the lancet body arm (8c) and move the lancet (8) towards the opening (40) of the lancet magazine so that the lancet tip (8) is exposed for the lancing operation. This sterile protection (9) can additionally undertake the function of securing the lancets (8) in the lancet magazine (7) while the lancet magazine (7) is in use, i.e., is inserted into a lancing aid but also outside a lancing aid. In this connection the sterile protection (9) secures the lancets (8) against unintentional protrusion from the openings (40) when a small force is exerted, e.g., by dropping the lancet magazine (7).

FIG. 3B shows the lancet magazine (7) after the extension process where the lancet tip (8a) of the lancet (8) at maximum excursion does not project from the lancet magazine (7). The maximum excursion is for example reached during the regular drive of the lancet (8) in a lancing aid (not shown here) as is carried out for a common lancing process in order to puncture the skin of a patient for blood collection.

Figure 4A:
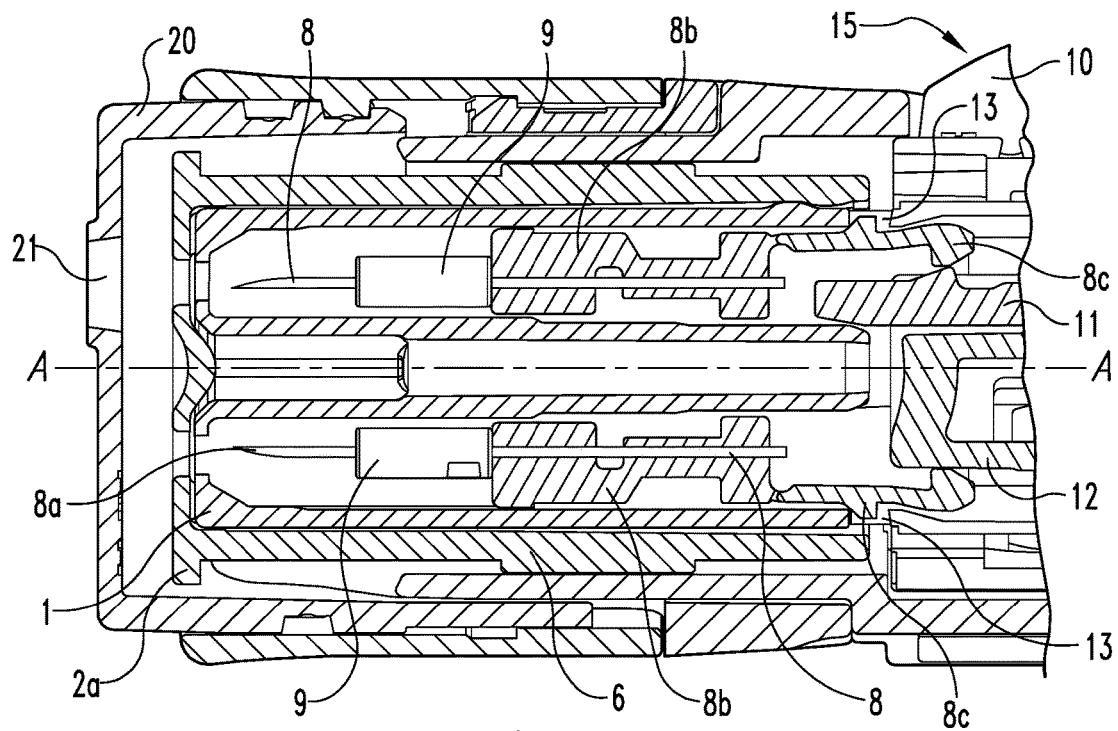
FIG. 4A is a sectional view of a lancet magazine fitted into a lancing aid which has a removable protective cap in a non-extended state in a longitudinal section along the line of intersection A-A.
Figure 4B:
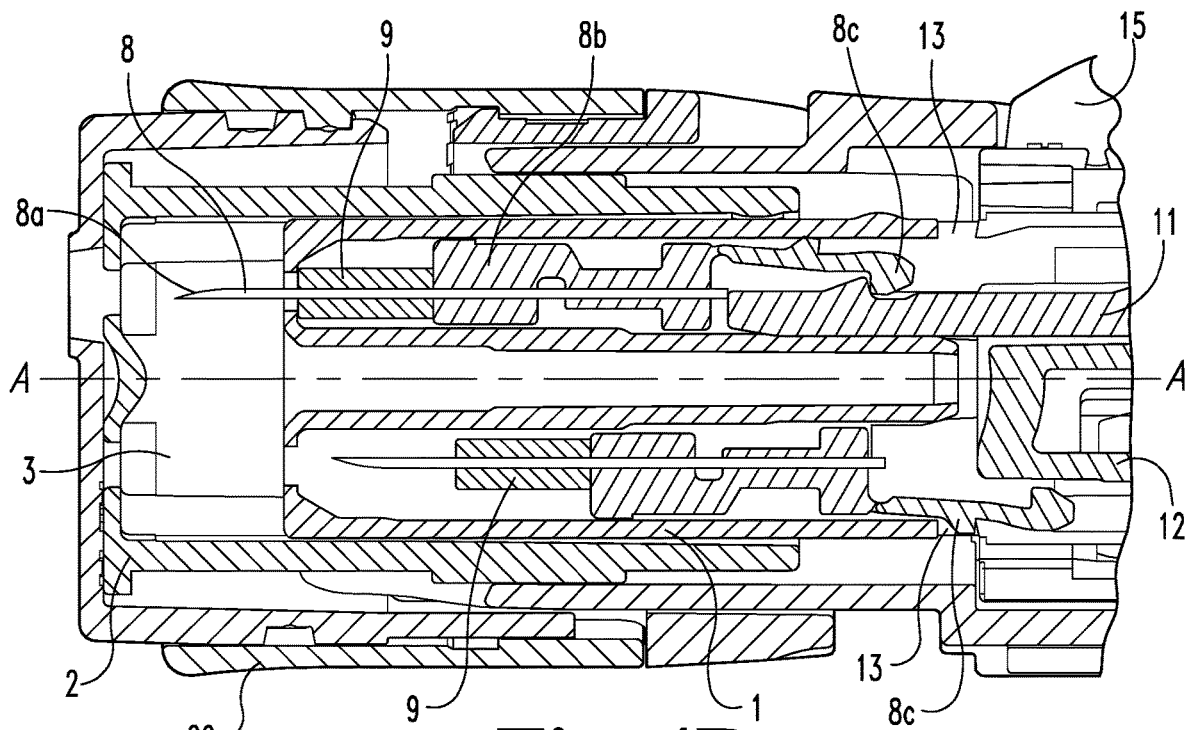
FIG. 4B is a longitudinal sectional view along the line of intersection A-A of a lancet magazine in an extended state fitted into a lancing aid with a removable protective cap where the protective cap no longer latch with the lancing aid.

This state is shown in FIG. 4B in which the lancet magazine (7) is shown integrated into a lancing aid (15) after the lancet magazine housing (1) has been extended. In this case it is indeed possible to correctly couple the lancet magazine (7) to the housing (10) of the lancing aid (15) which means that the means for locking together the lancet magazine (7) and lancing aid (15) are not impaired. It is also still possible to couple the plunger (11) so that the lancet (8) is moved within the lancet housing (1) to the distal end of the lancet magazine (7a) but cannot emerge from the lancet magazine that has been extended by the extension unit (2) and consequently no lancing operation can be executed. However, in this embodiment it is not possible to attach the finger cap (20) in such a manner that the housing of the lancing aid (10) can lock with the finger cap (20).

This is different in the non-extended state of the lancet magazine (7) which is correctly incorporated into a lancing aid (15) as shown in FIG. 4A. In this case the lancet magazine (7) is also inserted and centered in the lancing aid (15) by means of a pin (12) so that the plunger (11) can interact in a lancing operation with the lancet via the lancet body arm (8c) in such a manner that the lancet (8) in the magazine is moved in a guided manner and the lancet tip (8a) is moved out of the lancing aid (15) through the opening (21) of the finger cap (20). In this case the pin (12) is inserted in such an asymmetric manner into the lancet magazine (7) that it does not impede the movement of the plunger (11) with the lancet (8) that is currently located in front of the opening of the finger cap (21), but protects all other lancets (8) in the magazine against unintentional movement. This movement protection is achieved in that the lancet body arms (8c) of the other lancets (8) are located in a groove (13) of the lancet magazine (1) (or alternatively between the lancet magazine (1) and lancing aid (15)). The pin projects beyond a part of the lancet body arms (8c) to such an extent that even when force is exerted on the lancing aid (15) or onto the lancet magazine (7), the lancets (8) cannot shift from their position because the lancet body arm (8a) is clamped in the groove (13) between the pin (12) and the lancet magazine housing (1).

Figure 5A:
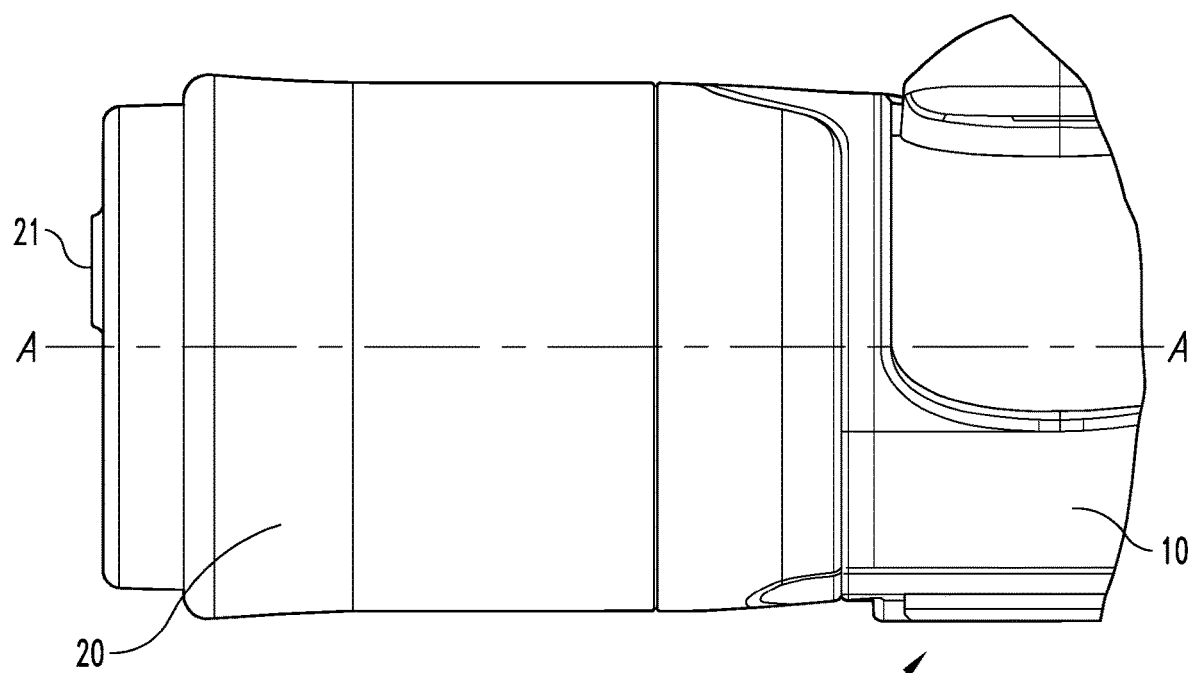
FIG. 5A is a side view of a lancing aid with a finger cap which is correctly locked into place because the inserted lancet magazine is not in an extended state.
Figure 5B:
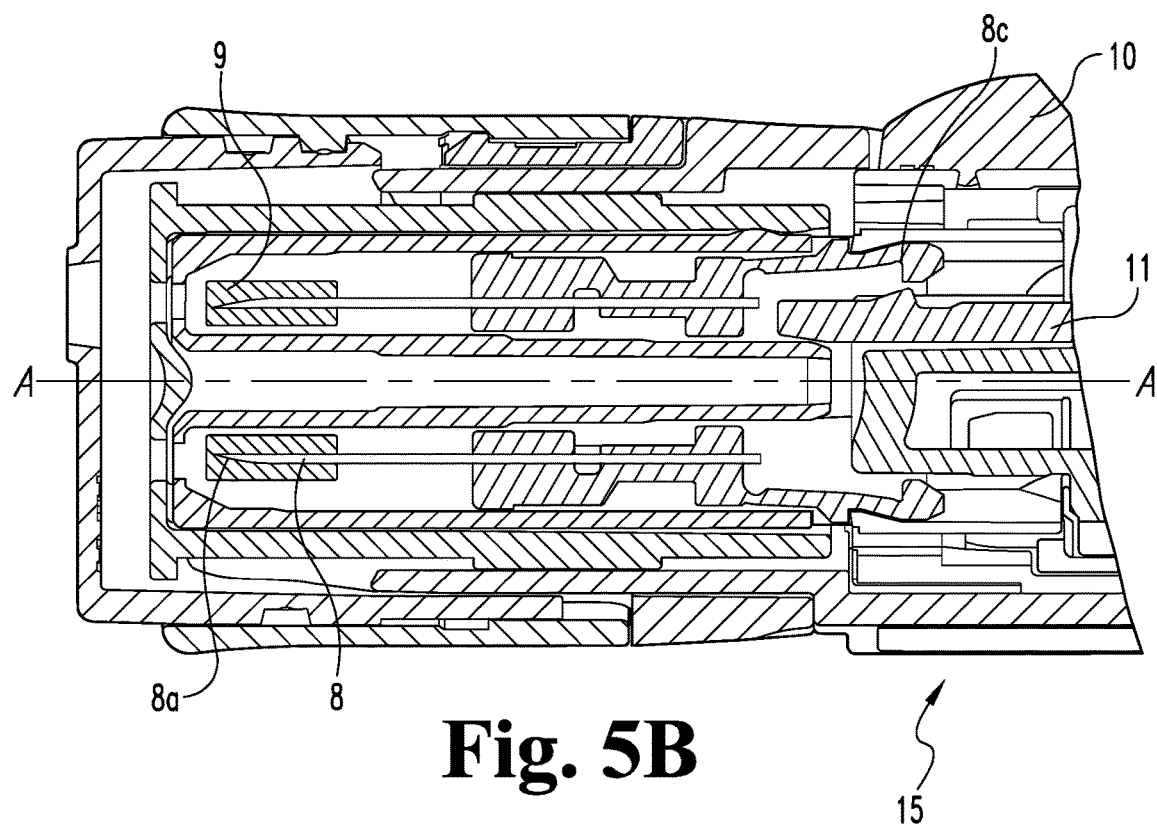
FIG. 5B is a longitudinal section through a lancing aid from FIG. 5A with a finger cap and inserted lancet magazine in a non-extended state along the line of intersection A-A.
Figure 5C:
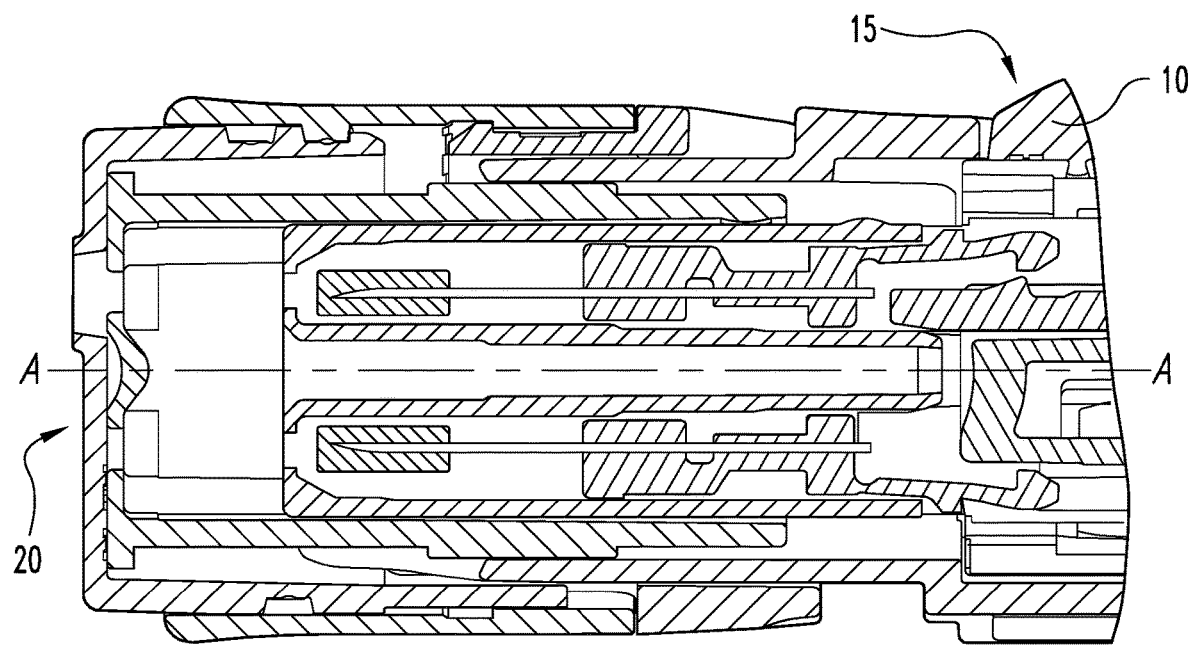
FIG. 5C is a longitudinal section of a lancing aid with an inserted lancet magazine after extension and attached finger cap which cannot be correctly locked with the lancing aid (line of intersection A-A)
Figure 5D:
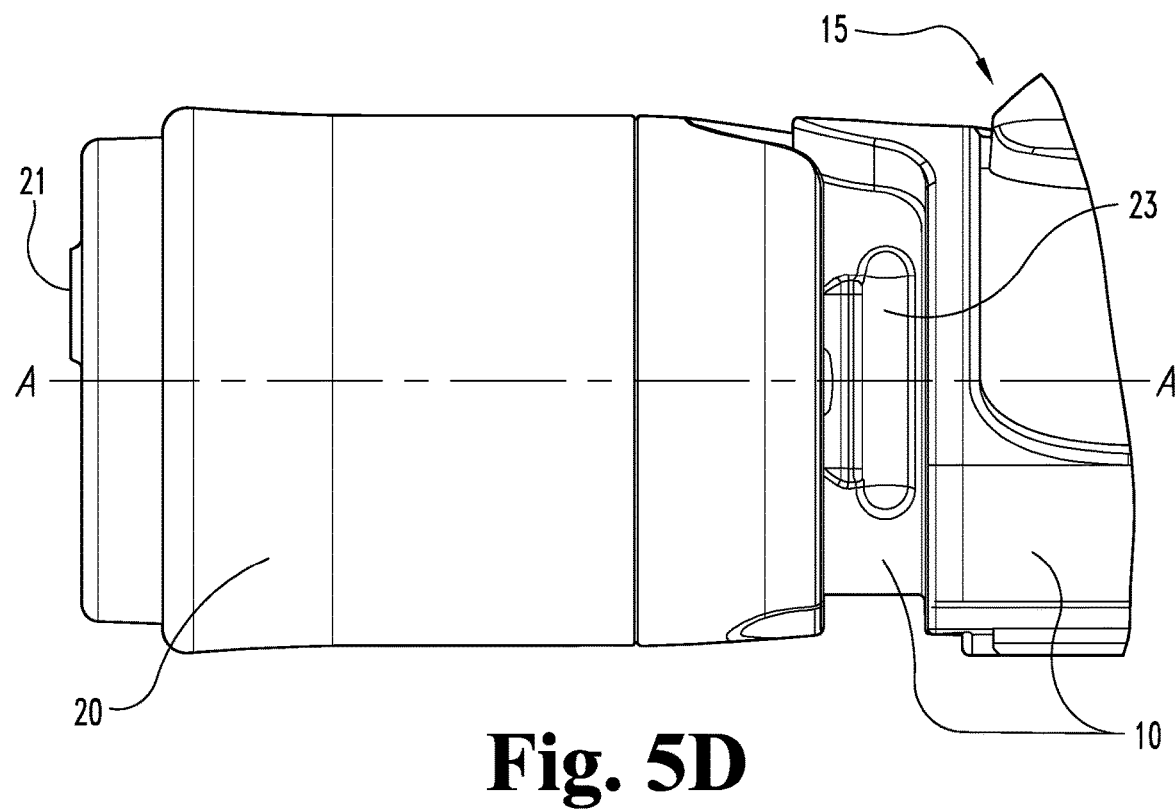
FIG. 5D is a side view of a lancing aid with a finger cap which cannot latch with the lancing aid because the lancet magazine is in an extended state.

FIGS. 5A to 5D show the lancet magazine (7) incorporated in a lancing aid (15) with an attached finger cap (20) in the unextended state of the lancet magazine (7) in FIGS. 5A and 5B and in the extended state of the lancet magazine (7) in FIGS. 5C and 5D. The lancing aid (15) with a properly attached finger cap (20) is shown in Fig. A where the finger cap (20) is locked with the housing (10) of the lancing aid (15) in such a manner that it optically forms one unit. A section along the line of intersection A-A of this assembled lancing aid (15) is shown in FIG. 5B. This in turn shows that the lancet magazine (7) interacts with the lancing aid (15) in such a manner that the plunger (11) of the lancing aid (15) can be brought into contact with the lancet body arm (8c) in such a manner that the tip (8a) of the lancet (8) can emerge in a guided manner from the opening (21) of the lancing aid (15) or the finger cap (20).

FIGS. 5B and 5C show the state in which an extended lancet magazine (7) is inserted into a lancing aid (15) where the magazine (7) can interact with the lancing aid (15) but the finger cap (20) can no longer be correctly placed on the lancing aid. This is shown particularly well in FIG. 5D because the depression in the housing (10) of the lancing aid (15) is exposed and is not reached by the finger cap (20) so that only a loose connection between the finger cap (20) and lancing aid (15) is achieved which does not hold when the lancing aid (15) alone is gripped in its housing (10) and held in the direction of the distal end (7a). In this state it becomes apparent to the operator that the magazine (7) cannot be correctly assembled with the lancing aid (15) including the finger cap (20) and must consequently have been used.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS 1 housing of the lancet magazine
2 extension unit
2a grip edge
2b notch on extension unit
3a cavity boundary
4 latch arm
4a latch arm inside 10 4b notch on latch arm
5 side slot
5a distal end of side slot
5b proximal end of side slot
6 guide
7 lancet magazine
7a distal end (lancet magazine)
7b proximal end (lancet magazine)
8 lancet
8a lancet tip
8b lancet body
8c lancet body arm
9 sterile protection
10 housing of lancing aid
11 plunger
12 pin
13 groove
15 lancing aid
20 finger cap
21 opening of finger cap
23 depression
30 proximal opening of lancet magazine
40 distal opening of lancet magazine
50 optical mark

What is claimed is:

1. A method for avoiding re-use of a lancet magazine, comprising;
   (a) inserting a lancet magazine having a plurality of lancets into a lancing aid;
   (b) performing at least one lancing operation with at least one lancet of the plurality of lancets;
   (c) removing the lancet magazine from the lancing aid; and
   (d) moving an extension unit of the lancet magazine into an extended state which increases the length of the lancet magazine and thereby prevents the lancets from emerging from the lancet magazine, whereby, in the extended state, the lancet magazine is configured for reinsertion into the lancing aid without impairing the lancing aid.

2. The method of claim 1, wherein step (d) is executed automatically during step (c).

3. The method of claim 1, further comprising reinserting the lancet magazine into the lancing aid after step (d) without impairing the lancing aid.

4. The method of claim 3, wherein the extension unit remains in the extended state during the reinserting of the lancet magazine into the lancing aid.

5. The method of claim 4, further comprising, after the lancet magazine has been reinserted into the lancing aid, triggering a lancing mechanism of the lancing aid and thereby moving one of the lancets within the lancet magazine.

6. The method of claim 1, wherein step (d) comprises locking the extension unit in the extended state.

7. The method of claim 6, wherein the locking is done via notches located on the extension unit and a housing of the lancet magazine.

8. The method of claim 6, wherein the locking is done via a groove located on one of the extension unit and a housing of the lancet magazine and a notch located on the other of the extension unit and the housing.

9. The method of claim 1, wherein step (d) occurs while a user manually removes the lancet magazine from the lancing aid.

10. The method of claim 1, further comprising providing the extension unit and a housing of the lancet magazine as cylindrically shaped and movably connected to one another.

11. The method of claim 10, wherein the extension unit and the housing are provided as a concentric arrangement and the housing fits at least partially within the extension unit.

12. The method of claim 1, wherein step (d) causes a housing of the lancet magazine to extend from the extension unit.

13. The method of claim 1, further comprising aligning the extension unit and the housing parallel to one another.

14. The method of claim 13, wherein the extension unit and the housing remain parallel to one another during step (d).

* * * * *